(12) United States Patent
Desai et al.

(10) Patent No.: US 12,208,230 B2
(45) Date of Patent: Jan. 28, 2025

(54) FLUID CONNECTOR ASSEMBLY THAT SEALS FLOW PATHS WHEN THE CONNECTORS ARE DISCONNECTED

(71) Applicant: CareFusion 303, Inc., San Diego, CA (US)

(72) Inventors: Aman Desai, Karnataka (IN); Abin Austin, Kerala (IN); Mohammed Mehtab Khan, Karnataka (IN)

(73) Assignee: CAREFUSION 303, INC., San Diego, CA (US)

( * ) Notice: Subject to any disclaimer, the term of this patent is extended or adjusted under 35 U.S.C. 154(b) by 90 days.

(21) Appl. No.: 17/983,894

(22) Filed: Nov. 9, 2022

(65) Prior Publication Data

US 2024/0151338 A1    May 9, 2024

(51) Int. Cl.
*A61M 39/26*    (2006.01)
*A61M 39/10*    (2006.01)
*F16L 37/35*    (2006.01)

(52) U.S. Cl.
CPC ............ *A61M 39/26* (2013.01); *A61M 39/10* (2013.01); *A61M 2039/1027* (2013.01);
(Continued)

(58) Field of Classification Search
CPC ............ A61M 39/26; A61M 2039/263; A61M 2039/267; A61M 2039/268;
(Continued)

(56) References Cited

U.S. PATENT DOCUMENTS

| 5,492,147 A | * | 2/1996 | Challender | F16L 37/28 |
| | | | | 604/905 |
| 5,713,856 A | | 2/1998 | Eggers et al. | |

(Continued)

FOREIGN PATENT DOCUMENTS

| EP | 1678070 A2 | 7/2006 |
| EP | 1517723 B1 | 1/2007 |

(Continued)

OTHER PUBLICATIONS

Bangert, Bill, "Shorter times to blood transfusion associated with decreased death risk in trauma patients", Medical Xpress, Apr. 14, 2016, https://medicalxpress.com/news/2016-04-shorter-blood-transfusion-decreased-death.html.

(Continued)

*Primary Examiner* — David Colon-Morales
(74) *Attorney, Agent, or Firm* — Morgan, Lewis & Bockius LLP

(57) ABSTRACT

Fluid connector assemblies that seal off fluid paths in the respective connectors are disclosed. When connectors of a fluid connector assembly are connected to each other, respective compressible members in the connectors are displaced, allowing downstream fluid passage through the fluid connector assembly. The connectors maintain a connection by a snap mechanism that provides a threshold retention force. When an external force greater than the threshold force is applied to the fluid connector assembly, the snap mechanism may no longer maintain the connectors together, causing the connectors to decouple from each other. However, each of the compressible members can return to their respective original positions and shapes to seal off respective fluid paths in the connectors, thus preventing further downstream and upstream flow through the (Continued)

fluid connector assembly and limiting or preventing fluid loss.

20 Claims, 8 Drawing Sheets

(52) U.S. Cl.
CPC ............... *A61M 2039/1061* (2013.01); *A61M 2039/263* (2013.01); *A61M 2039/267* (2013.01); *A61M 2205/0216* (2013.01); *F16L 37/35* (2013.01)

(58) Field of Classification Search
CPC .......... A61M 2205/0216; A61M 39/10; A61M 2039/1061; A61M 2039/1027; A61M 2039/1072; A61M 2039/1066; F16L 37/35
See application file for complete search history.

(56) References Cited

U.S. PATENT DOCUMENTS

| | | | |
|---|---|---|---|
| 5,820,614 A * | 10/1998 | Erskine | F16L 55/1007 604/905 |
| 6,874,522 B2 | 4/2005 | Anderson et al. | |
| 7,004,934 B2 * | 2/2006 | Vaillancourt | A61M 39/26 604/533 |
| 7,040,598 B2 | 5/2006 | Raybuck | |
| 7,044,441 B2 * | 5/2006 | Doyle | A61M 39/26 251/149.6 |
| 7,153,296 B2 | 12/2006 | Mitchell | |
| 7,350,764 B2 | 4/2008 | Raybuck | |
| 7,396,051 B2 * | 7/2008 | Baldwin | A61M 39/26 604/905 |
| 7,631,660 B2 * | 12/2009 | deCler | F16L 37/098 137/614.05 |
| 7,658,205 B1 * | 2/2010 | Edelman | A61M 39/1011 251/149.6 |
| 7,763,013 B2 | 7/2010 | Baldwin et al. | |
| 7,766,394 B2 | 8/2010 | Sage et al. | |
| 7,794,675 B2 | 9/2010 | Lynn | |
| 7,803,139 B2 | 9/2010 | Fangrow, Jr. | |
| 7,803,140 B2 | 9/2010 | Fangrow, Jr. | |
| 7,815,614 B2 | 10/2010 | Fangrow, Jr. | |
| 7,918,243 B2 | 4/2011 | Diodati et al. | |
| 7,998,134 B2 | 8/2011 | Fangrow et al. | |
| 8,123,738 B2 | 2/2012 | Vaillancourt | |
| 8,142,418 B2 | 3/2012 | McMichael et al. | |
| 8,211,069 B2 | 7/2012 | Fangrow, Jr. | |
| 8,262,628 B2 | 9/2012 | Fangrow, Jr. | |
| 8,361,408 B2 | 1/2013 | Lynn | |
| 8,480,968 B2 | 7/2013 | Lynn | |
| 8,777,908 B2 | 7/2014 | Fangrow, Jr. | |
| 8,777,909 B2 | 7/2014 | Fangrow, Jr. | |
| 8,795,256 B1 | 8/2014 | Smith | |
| 8,888,758 B2 | 11/2014 | Mansour | |
| 8,899,267 B2 | 12/2014 | Diodati et al. | |
| 8,910,919 B2 | 12/2014 | Bonnal et al. | |
| 8,974,425 B2 * | 3/2015 | Tachizaki | F16L 37/30 604/905 |
| 8,974,437 B2 | 3/2015 | Williams et al. | |
| 9,039,047 B2 * | 5/2015 | Imai | A61J 1/2096 285/402 |
| 9,114,242 B2 | 8/2015 | Fangrow et al. | |
| 9,126,028 B2 | 9/2015 | Fangrow et al. | |
| 9,126,029 B2 | 9/2015 | Fangrow et al. | |
| 9,168,366 B2 * | 10/2015 | Fangrow | A61M 39/26 |
| 9,192,753 B2 | 11/2015 | Lopez et al. | |
| 9,234,616 B2 | 1/2016 | Carrez et al. | |
| 9,358,379 B2 | 6/2016 | Fangrow, Jr. | |
| 9,409,007 B2 * | 8/2016 | Yeh | A61M 39/26 |
| 9,433,769 B2 | 9/2016 | Bayly | |
| 9,468,749 B2 | 10/2016 | Mansour et al. | |
| 9,492,649 B2 * | 11/2016 | Carrez | A61M 39/26 |
| 9,636,492 B2 | 5/2017 | Fangrow, Jr. | |
| 9,724,504 B2 | 8/2017 | Fangrow, Jr. et al. | |
| 9,724,505 B2 | 8/2017 | Williams et al. | |
| 9,861,805 B2 | 1/2018 | Dennis et al. | |
| 9,933,094 B2 * | 4/2018 | Fangrow | A61M 39/18 |
| 9,974,939 B2 | 5/2018 | Fangrow, Jr. | |
| 9,974,940 B2 | 5/2018 | Fangrow, Jr. | |
| 10,029,086 B2 | 7/2018 | Nowak et al. | |
| 10,156,306 B2 | 12/2018 | Fangrow | |
| 10,173,045 B2 | 1/2019 | Mansour | |
| 10,179,203 B1 | 1/2019 | Huslage et al. | |
| 10,286,203 B2 * | 5/2019 | Gagliardoni | A61M 39/26 |
| 10,315,025 B2 | 6/2019 | Phillips et al. | |
| 10,322,274 B2 * | 6/2019 | Ueda | A61M 39/24 |
| 10,398,887 B2 | 9/2019 | Fangrow, Jr. et al. | |
| 10,441,507 B2 | 10/2019 | Sanders | |
| 10,518,078 B2 | 12/2019 | Stjernberg Bejhed et al. | |
| 10,569,073 B2 | 2/2020 | Hallisey et al. | |
| 10,625,068 B2 | 4/2020 | Leuthardt et al. | |
| 10,655,768 B2 | 5/2020 | Jones et al. | |
| 10,697,570 B2 | 6/2020 | Fangrow | |
| 10,744,315 B2 * | 8/2020 | Sanders | A61J 1/2089 |
| 10,842,982 B2 | 11/2020 | Fangrow, Jr. | |
| 10,857,346 B2 | 12/2020 | Dennis et al. | |
| 10,864,362 B2 | 12/2020 | Jones et al. | |
| 10,881,847 B2 | 1/2021 | Lynn | |
| 11,123,534 B2 * | 9/2021 | Chen | A61M 39/10 |
| 11,168,818 B2 | 11/2021 | Fangrow | |
| 11,207,514 B2 * | 12/2021 | Kakinoki | A61M 39/10 |
| 11,235,135 B2 * | 2/2022 | Tsai | A61M 39/22 |
| 11,273,297 B2 | 3/2022 | Kakinoki | |
| 11,298,518 B2 * | 4/2022 | Fuchs | A61M 39/26 |
| 11,484,471 B2 | 11/2022 | Sanders | |
| 11,491,084 B2 * | 11/2022 | Ueda | A61M 39/14 |
| 2004/0215158 A1 | 10/2004 | Anderson | |
| 2005/0090805 A1 | 4/2005 | Shaw et al. | |
| 2006/0129109 A1 | 6/2006 | Shaw et al. | |
| 2007/0088292 A1 | 4/2007 | Fangrow, Jr. | |
| 2007/0088293 A1 | 4/2007 | Fangrow, Jr. | |
| 2007/0088294 A1 | 4/2007 | Fangrow, Jr. | |
| 2007/0225635 A1 | 9/2007 | Lynn | |
| 2008/0039803 A1 | 2/2008 | Lynn | |
| 2009/0001720 A1 * | 1/2009 | Cheon | A61M 39/26 285/317 |
| 2011/0106046 A1 | 5/2011 | Hiranuma | |
| 2014/0249487 A1 | 9/2014 | Lynn | |
| 2014/0330254 A1 | 11/2014 | Rosenberger et al. | |
| 2016/0000363 A1 | 1/2016 | Jones et al. | |
| 2018/0200147 A1 | 7/2018 | Sanders | |
| 2019/0184152 A1 | 6/2019 | Kakinoki | |
| 2019/0282797 A1 | 9/2019 | Tsai | |
| 2020/0113784 A1 | 4/2020 | Lopez et al. | |
| 2020/0179672 A1 | 6/2020 | Kakinoki | |
| 2020/0215319 A1 | 7/2020 | Fangrow, Jr. et al. | |
| 2020/0284385 A1 | 9/2020 | Fangrow | |
| 2020/0323734 A1 | 10/2020 | Ueda et al. | |
| 2020/0338331 A1 | 10/2020 | Sanders | |
| 2021/0069484 A1 | 3/2021 | Tsai | |
| 2021/0077803 A1 | 3/2021 | Lynn | |
| 2021/0252267 A1 | 8/2021 | Fangrow, Jr. | |
| 2021/0388926 A1 | 12/2021 | Martin et al. | |
| 2021/0393938 A1 | 12/2021 | Lynn et al. | |
| 2022/0260189 A1 | 8/2022 | Deuse | |
| 2022/0282814 A1 | 9/2022 | Fangrow | |
| 2023/0355946 A1 * | 11/2023 | Kuriyama | A61M 39/26 |

FOREIGN PATENT DOCUMENTS

| | | |
|---|---|---|
| EP | 1622675 B1 | 8/2009 |
| EP | 2144634 A1 | 1/2010 |
| EP | 2298407 A1 | 3/2011 |
| EP | 2694132 A1 | 2/2014 |
| EP | 2562456 B1 | 6/2014 |
| EP | 2782633 A1 | 10/2014 |
| EP | 1842002 B1 | 4/2015 |
| EP | 2736582 B1 | 5/2015 |
| EP | 2089094 B1 | 1/2016 |
| EP | 2219721 B1 | 12/2017 |

(56) References Cited

FOREIGN PATENT DOCUMENTS

| | | | |
|---|---|---|---|
| EP | 2753396 B1 | 12/2017 | |
| EP | 2736584 B1 | 4/2018 | |
| EP | 3305361 A1 | 4/2018 | |
| EP | 2271398 B1 | 11/2018 | |
| EP | 2480281 B1 | 11/2018 | |
| EP | 2790750 B1 | 11/2018 | |
| EP | 2331191 B1 | 3/2019 | |
| EP | 3079756 B1 | 3/2019 | |
| EP | 2121114 B1 | 5/2019 | |
| EP | 2719419 B1 | 5/2019 | |
| EP | 2956204 B1 | 8/2019 | |
| EP | 3421077 B1 | 8/2019 | |
| EP | 3530313 A1 | 8/2019 | |
| EP | 3538201 A1 | 9/2019 | |
| EP | 3570807 A1 | 11/2019 | |
| EP | 3570809 A1 | 11/2019 | |
| EP | 2536463 B1 | 4/2020 | |
| EP | 3381505 B1 | 5/2020 | |
| EP | 3538201 B1 | 5/2020 | |
| EP | 1904152 B1 | 12/2020 | |
| EP | 2150307 B1 | 12/2020 | |
| EP | 3313490 B1 | 1/2021 | |
| EP | 3760275 A1 | 1/2021 | |
| EP | 3851155 A1 | 7/2021 | |
| EP | 3517164 B1 | 9/2021 | |
| EP | 3954355 A1 | 2/2022 | |
| EP | 3960229 A1 * | 3/2022 | ............ A61M 39/10 |
| EP | 3973044 A1 | 3/2022 | |
| EP | 3305361 B1 | 5/2022 | |
| EP | 3134052 B1 | 8/2022 | |
| EP | 3530313 B1 | 8/2022 | |
| WO | WO-2021099437 A1 | 5/2021 | |
| WO | WO-2021180675 A1 | 9/2021 | |
| WO | WO-2021252197 A1 | 12/2021 | |
| WO | WO-2022042956 A1 | 3/2022 | |
| WO | WO-2022149339 A1 | 7/2022 | |
| WO | WO-2022207560 A1 | 10/2022 | |

OTHER PUBLICATIONS

Icumedical, "ChemoClave™ Needlefree Close System Transfer Device (CSTD)", date unknown, https://www.icumed.com/products/oncology/closed-system-transfer-devices/chemoclave.

Icumedical, "ChemoLock™ Needlefree Closed System Transfer Device (CSTD)", date unknown, https://www.icumed.com/products/oncology/closed-system-transfer-devices/chemolock.

Ivteam, "Force-activated separation IV connectors", 2022, Retrieved from the internet https://www.ivteam.com/intravenous-literature/force-activated-separation-iv-connectors/ [Last retrieved Jan. 13, 2023].

Lineus Medical, SafeBreak Product Features and Benefits Brochure, May 2021, mkg 0058 5/21 Rev. 02.

Przen, "Lineus Medical Goes International, Signs ONEY for Distribution in Korea", PRZen Online Press Release Distribution, PrZen/33448014, MKG-0130 Rev 00, Retrieved from the internet https://przen.com/pr/lineus-medical-goes-international-signs-oney-for-distribution-in-korea-przen-33448014 [Last retrieved Jan. 13, 2023].

Rickard, et al., "Securing All intraVenous devices Effectively in hospitalised patients—the SAVE trial: study protocol for a multicentre randomised controlled trial", BMJ Open, Sep. 23, 2015;5(9):e008689, doi: 10.1136/bmjopen-2015-008689. PMID: 26399574; PMCID: PMC4593168.

Tada Group AB, LinkedIn Post "ReLink granted patent in Japan", LinkedIn, Mar. 2022, retrieved from the internet https://se.linkedin.com/company/tadamedical?trk=public_post_reshare_feed-actor-image&original_referer= [Last retrieved Mar. 2022].

Tribology, "Coefficient of friction, Rolling resistance and Aerodynamics", date unknown, https://www.tribology-abc.com/abc/cof.htm.

International Search Report and Written Opinion for Application No. PCT/US2023/032211, dated Dec. 21, 2023, 9 pages.

\* cited by examiner

FLUID CONNECTOR ASSEMBLY THAT SEALS FLOW PATHS WHEN THE CONNECTORS ARE DISCONNECTED

TECHNICAL FIELD

The present disclosure relates generally to medical fluid connectors and, more particularly, to a fluid connector assembly that includes medical connectors that decouple with each other due to an applied force, with each medical connector designed to automatically seal off their respective fluid paths. The decoupling may be due to intentional or unintentional separation between the medical connectors.

BACKGROUND

Peripheral intravenous ("PIVC") catheters are medical tools inserted into peripheral veins of patients to deliver medical fluid to the patients. In an example application, the medical fluid is delivered to the patient, and a medical professional subsequently removes the PIVC catheter from the patient. Often, however, these catheters are unintentionally dislodged. For example, catheter lines receiving an unintended or unexpected pulling force can pull the IV tubing, which pulls the catheter out of the patient. In other instances, catheters are accidentally removed from patients and medical professionals. Unintended or unexpected dislodgement can lead to patient blood loss, IV fluid loss, and IV fluid delivery delay.

SUMMARY

In accordance with at least some embodiments disclosed herein is the realization that unintended dislodgement or disconnection of a medical connection, such as a medical fluid line, can result in injury to a patient or a medical professional, such as by depriving the patient of a medicament, increasing the potential for infection to the patient, and exposing the medical professional to medicaments.

Aspects of the present disclosure provide fluid connector assemblies with medical connectors, each of which include one or more fluid paths, that respond to unintentional or unexpected external forces by decoupling from each other and sealing off their respective fluid paths. The decoupling may include automatic decoupling using bellows or other elastically compressible member that decompress and return to their original shape external forces are no longer acting upon them. Beneficially, fluid connector assemblies described herein can limit or prevent patient blood loss, IV fluid loss, infection, and medical delivery delays.

Accordingly, aspects of the present disclosure provide a fluid connector assembly comprising a first connector, comprising: a first housing comprising a cavity, a post disposed in the first housing, the post comprising an opening, and a compressible member surrounding the post; and a second connector configured to couple with the first connector, the second connector comprising: a second housing, and a plate coupled with the second housing, wherein when the second housing is positioned in the cavity, the plate displaces the compressible member and exposes the opening.

Some instances of the present disclosure provide a connector suitable for use with intravenous applications, the connector comprising: a housing; a post disposed within the housing, the post defining a channel; an opening formed in the post, the opening fluidly connected to the channel; a compressible member surrounding the post, wherein: responsive to an external force displacing the compressible member, the compressible member uncovers the opening, and when the external force is removed, the compressible member seals the opening.

Some aspects of the present disclosure provide a fluid connector assembly suitable for use with intravenous applications, the connector comprising: a housing; a compressible member disposed in the housing; and a plate coupled with the housing, the plate defining an opening, wherein responsive to an external object entering the opening and displacing the compressible member, the compressible member uncovers the opening, and when the external object is removed, the compressible member seals the opening.

Some instances of the present disclosure provide methods for regulating fluid for an intravenous application, the methods comprising, by a fluid connector assembly: providing a first connector, the first connector comprising: a post that defines a channel, a first compressible member surrounding the post, an opening formed in the post, the opening fluidly connected to the channel, and a cavity; and receiving, at the cavity, a second connector, the second connector comprising: a plate, and a second compressible member; and displacing, by the plate, the first compressible member to uncover the opening; and displacing, by the post, the second compressible member, thereby allowing the fluid to pass through the opening.

Some instances of the present disclosure provide methods for regulating fluid, the methods comprising, by a connector: receiving, at a housing, an external force, the housing comprising a post that includes an opening; displacing, based on receiving the external force, a compressible member disposed in the housing; and uncovering, based on displacing the compressible member, the opening.

Some methods for regulating a fluid, the methods comprising, by a connector: receiving, at a housing, an external force, the housing comprising a plate that includes an opening; displacing, based on receiving the external force, a compressible member disposed in the housing; and uncovering, based on displacing the compressible member, the opening.

Accordingly, the present application addresses several operational challenges encountered during an unintended or unexpected catheter dislodgement.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures.

DETAILED DESCRIPTION

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments of the present disclosure may be disclosed or shown in the context of an IV set, such embodiments can be used in other fluid conveyance systems. Furthermore, various applications of such embodiments and modifications thereto, which may occur to those who are skilled in the art, are also encompassed by the general concepts described herein.

In accordance with some embodiments, the present disclosure includes various features and advantages of a fluid connector assembly with medical connectors that seal off their respective fluid paths when the medical connectors are decoupled from each other. The medical connectors may each include a compressible member that decompresses in response to the decoupling, thus providing an automatic sealing of the respective fluid paths.

Figure 1:
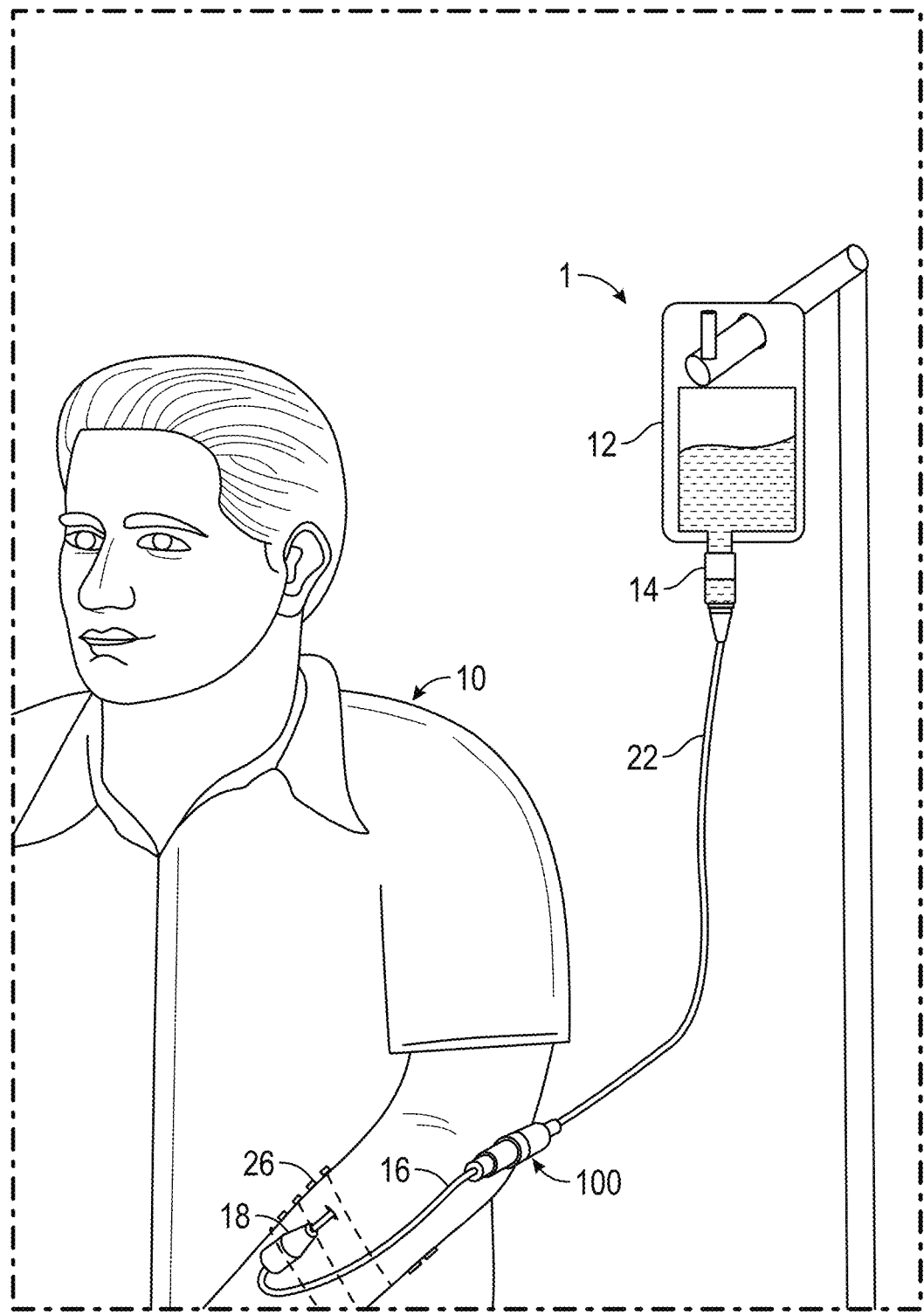
FIG. 1 illustrates an IV set coupled to a patient, in accordance with aspects of the present disclosure.

Referring now to the figures, FIG. 1 illustrates an IV set 1 coupled to a patient 10, in accordance with aspects of the present disclosure. The IV set 1 includes a medicament bag 12, a drip chamber 14, and tubing 22. The tubing 22 extends between the drip chamber 14 and a fluid connector assembly 100 of the IV set 1. To resist unintended dislodgement or disconnection of the tubing 16 or the catheter 18 from the patient, tape 26 is placed over the tubing 16 and the catheter 18, so that the tape 26 engages the tubing 16, the catheter 18, and the patient 10.

Figure 2:
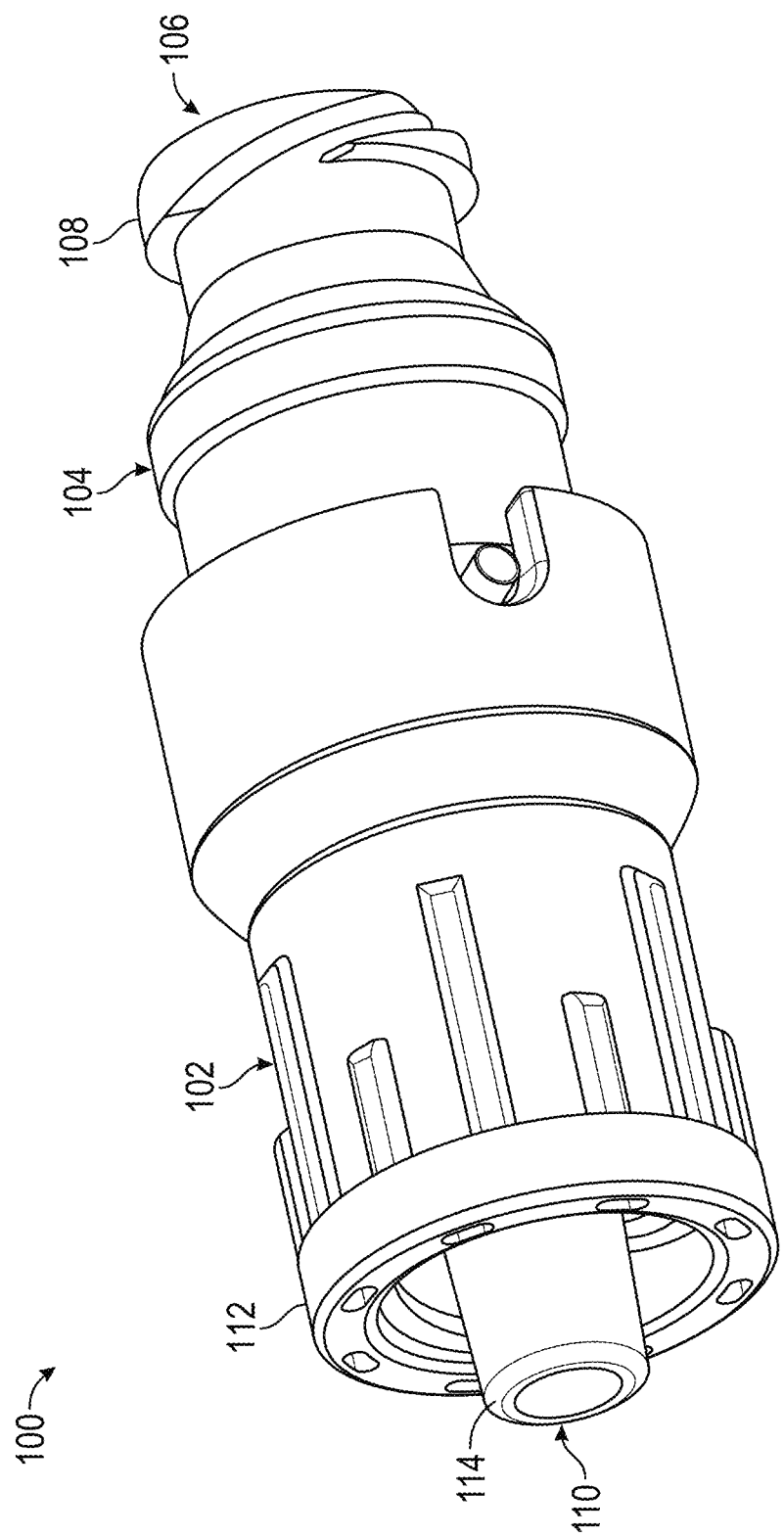
FIG. 2 illustrates a perspective view of a fluid connector assembly, in accordance with aspects of the present disclosure.

FIG. 2 illustrates a perspective view of a fluid connector assembly 100, in accordance with aspects of the present disclosure. The fluid connector assembly 100 is designed for use in medical applications, such as the IV set 1 (shown in FIG. 1) as well as other IV medical fluid delivery applications using catheters, including PIVC catheters, as non-limiting examples.

As shown, the fluid connector assembly 100 includes a connector 102 and a connector 104 coupled with the connector 102. The connector 102 and the connector 104 may be referred to as a first connector and a second connector, respectively. However, "first" and "second" may be interchangeable. Also, each of the connectors 102 and 104 may be referred to as medical connectors. When the connectors 102 and 104 are connected to each other as shown in FIG. 2, a fluid path for medical fluid is established by the fluid connector assembly 100.

In some embodiments, the connector 104 is connected to a medical fluid (not shown). Further, in some embodiments, the connector 102 is connected to a catheter line (not shown) that delivers the medical fluid to a catheter. In this regard, the connector 104 may include a fluid inlet 106 that acts as a fluid receiving location for the fluid connector assembly 100. Also, the connector 102 may include a fluid outlet 110 that acts as a fluid transmission location for the fluid connector assembly 100.

To facilitate the connection to the medical fluid, the connector 104 includes a luer 108. In some embodiments, the luer 108 is female luer designed to mate with a male connector that is connected to the medical fluid. To facilitate the connection to the catheter line, the connector 102 includes a luer 112. In some embodiments, the luer 112 is male luer designed to mate with a female connector that is connected to the catheter line. Also, each of the luers 108 and 112 may conform to standards established by the International Organization for Standards ("ISO") to improve patient safety, minimize medical fluid leakage, and reduce misconnection with other connection devices.

Additionally, the connector 102 includes a post 114 passing centrally, or at least approximately centrally, through the connector 102. The post 114 includes a channel that establishes the fluid outlet 110. As shown, the post 114 is cylindrical. However, other shapes are possible.

Figure 3:
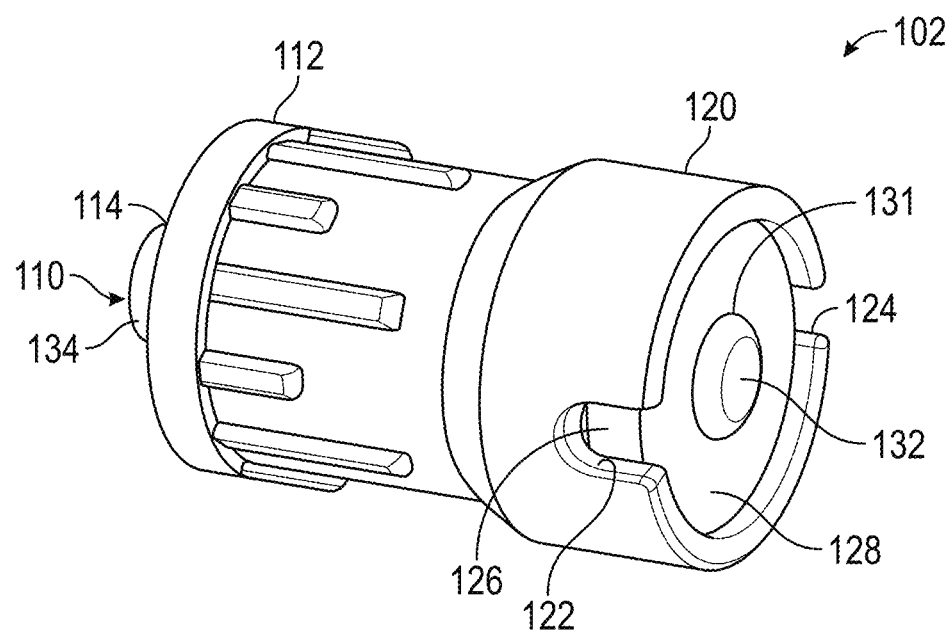
FIG. 3 illustrates a perspective view of the connector of the fluid connector assembly, in accordance with aspects of the present disclosure.

FIG. 3 illustrates a perspective view of the connector 102, showing additional features, in accordance with aspects of the present disclosure. The connector 102 includes a housing 120 integrated with the luer 112. The housing 120 includes a slot 122 and a slot 124, each of which is designed to facilitate proper connection between the connector 102 and the connector 104 (shown below). The housing 120 includes a hollow, or generally hollow, body that carries one or more components. For example, a compressible member 126 located in the housing 120. In some embodiments, the compressible member 126 includes a bellow that can elastically compress. Accordingly, the compressible member 126 can compress by an external force and subsequently return to its original, uncompressed form when the external force is removed. The compressible member 126 is designed to regulate fluid flow through the connector 102. This will be shown in detail below. The compressible member 126 includes an engagement surface 128 designed to engage a component of the connector 104. The engagement surface 128 provides a planar, or generally planar, surface that can be readily accessed for cleaning and disinfecting.

The engagement surface 128 includes an opening 131 through which the post 114 is positioned. The post 114 includes two ends opposite each other, with each end having a different configuration. For example, the post 114 includes a closed end 132 and an open end 134 opposite the closed end 132. The closed end 132 is covered by a surface formed from, for example, a material of the housing 120, while the open end 134 is uncovered and is integrated with the fluid outlet 110. As shown, the closed end 132 of the post 114 extends through the opening 131 of the engagement surface 128.

Figure 4:
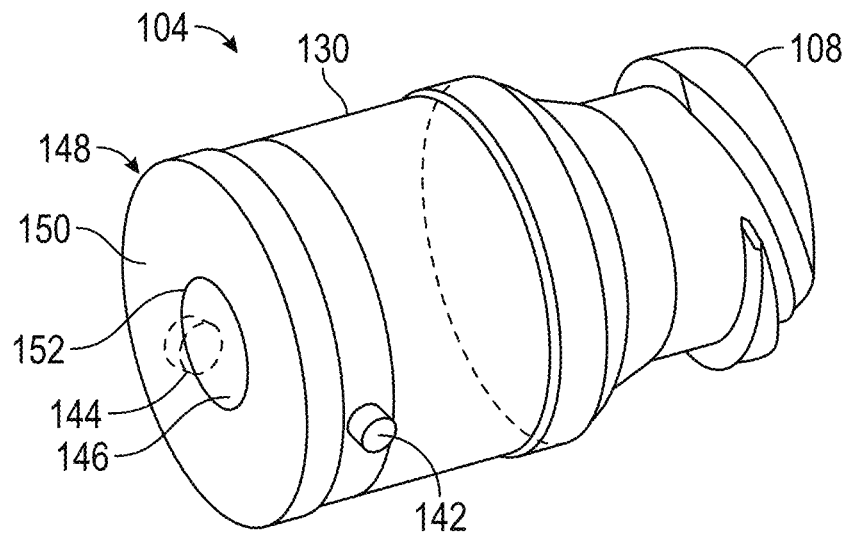
FIG. 4 illustrates a perspective view of the connector of the fluid connector assembly, in accordance with aspects of the present disclosure.

FIG. 4 illustrates a perspective view of the connector 104, showing additional features, in accordance with aspects of the present disclosure. The connector 104 includes a housing 130. The housing 120 (shown in FIG. 3) and the housing 130 may be referred to as a first housing and a second housing, respectively. However, "first" and "second" may be interchangeable. As shown, the housing 130 is integrated with the luer 108. The housing 130 includes a pin 142 and a pin 144, each of which act as a guide pin designed to facilitate proper connection between the connector 104 and the connector 102 (shown in FIG. 3). For example, to couple the connectors 102 and 104 together, the pins 142 and 144 are aligned with and positioned in the slots 122 and 124, respectively (shown in FIG. 3). The housing 130 includes a hollow, or generally hollow, body that carries one or more components. For example, the housing 130 includes a compressible member 146 located, or at least substantially located, in the housing 130. In some embodiments, the compressible member 146 includes a bellow that can elastically compress. Accordingly, the compressible member 146 can compress by an external force and subsequently return to its original, uncompressed form when the external force is removed. The compressible member 146 is designed to regulate fluid flow through the connector 104. This will be shown in detail below.

Additionally, the connector 104 includes a plate 148 connected to the housing 130. The connection means between the housing 130 and the plate 148 may include welding (e.g., ultrasonic welding, adhesives, or the like). Based on the connection, a seal is formed between the housing 130 and the plate 148 such that fluid does not flow between the housing 130 and the plate 148. The plate 148 includes an engagement surface 150 designed to engage the engagement surface 128 of the compressible member 126 (shown in FIG. 3). The engagement surface 150 provides a planar, or generally planar, surface that can be readily accessed for cleaning and disinfecting. Also, the plate 148 includes an opening 152 through which a portion of the compressible member 146 lies. As a result, when the connectors 102 and 104 are coupled together, the compressible member 146 may engage the closed end 132 of the post 114 (shown in FIG. 3). Also, based upon a portion of the compressible member 146 lying within the opening 152 of the plate 148, the plate 148 aligns the compressible member 146 within the housing 130.

Figure 5:
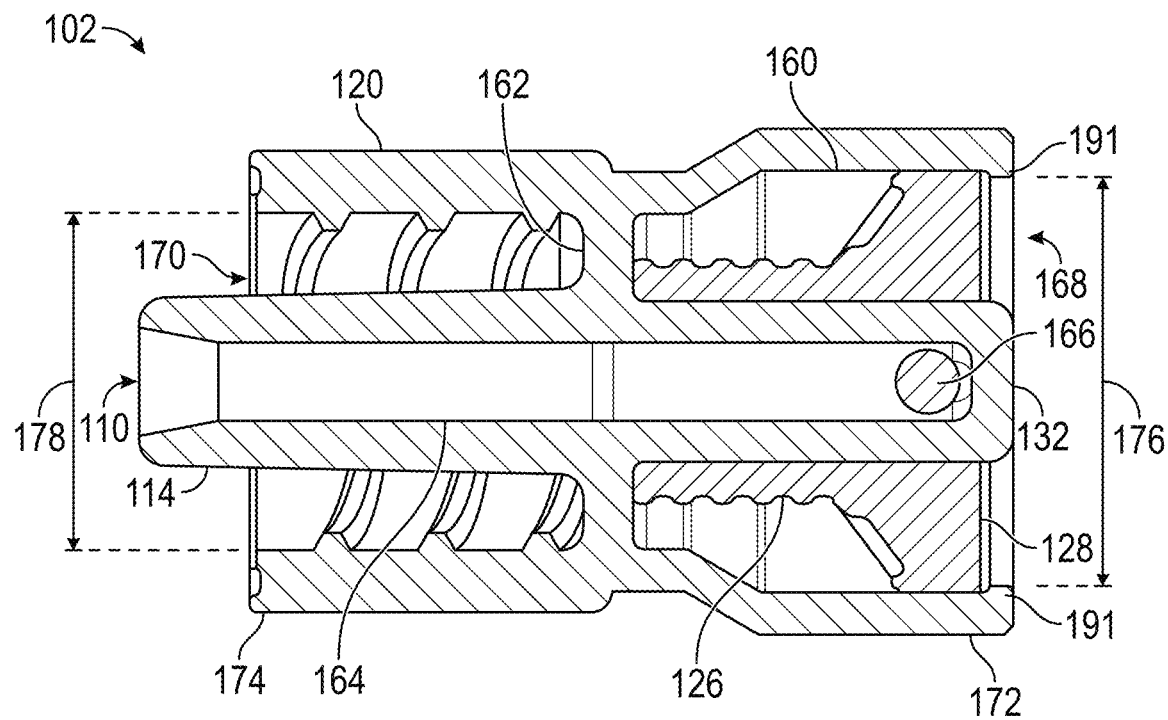
FIG. 5 illustrates a partial cross-sectional view of the connector of the fluid connector assembly, in accordance with aspects of the present disclosure.

FIG. 5 illustrates a partial cross-sectional view of the connector 102 of the fluid connector assembly 100, in accordance with aspects of the present disclosure. As shown, the compressible member 126 is located in a hollow portion of the housing 120 and is at least partially engaged an inner surface 160 of the housing 120. The post 114 is connected to the housing 120 by a wall 162. While the post 114 is integrated with the wall 162, the post 114, including a channel 164 of the post 114 that opens to the fluid outlet 110, passes through the wall 162. Also, the post 114 includes an opening 166, representative of one or more radial through holes formed in the post 114. The opening 166 is fluidly connected to the channel 164 and the fluid outlet 110. Any additional openings similar to that of the opening 166 that are formed in the post 114 may be fluidly connected to the channel 164 and may include any feature(s) shown and described for the opening 166. The wall 162 separate the housing 120 into two cavities. For example, the housing 120 includes a cavity 168 that is defined by the housing 120 and the post 114. As shown, the compressible member 126 surrounds the post 114 in the cavity 168. Also, the housing 120 includes a cavity 170 separated from the cavity 168 by the wall 162.

The housing 120 includes two opposing ends. As shown, the housing 120 includes an end 172 and an end 174 opposite the end 172. The end 172 of the housing 120 includes an inner diameter 176. Additionally, the end 174 of the housing 120 includes an inner diameter 178 having a dimension that is less than that of the inner diameter 176. Based on the disparate dimension of the inner diameters 176 and 178, in some embodiments, the cavity 168 may include a volume that is greater than that of the cavity 170.

Based on the position of the compressible member 126 shown in FIG. 5, the opening 166 is covered by the compressible member 126. In this regard, the compressible member 126 seals the opening 166 and fluid is prevented from flowing through the connector 102. For example, fluid entering the end 172 of the housing 120 is blocked from entering the opening 166 based on the position of the compressible member 126.

Figure 6:
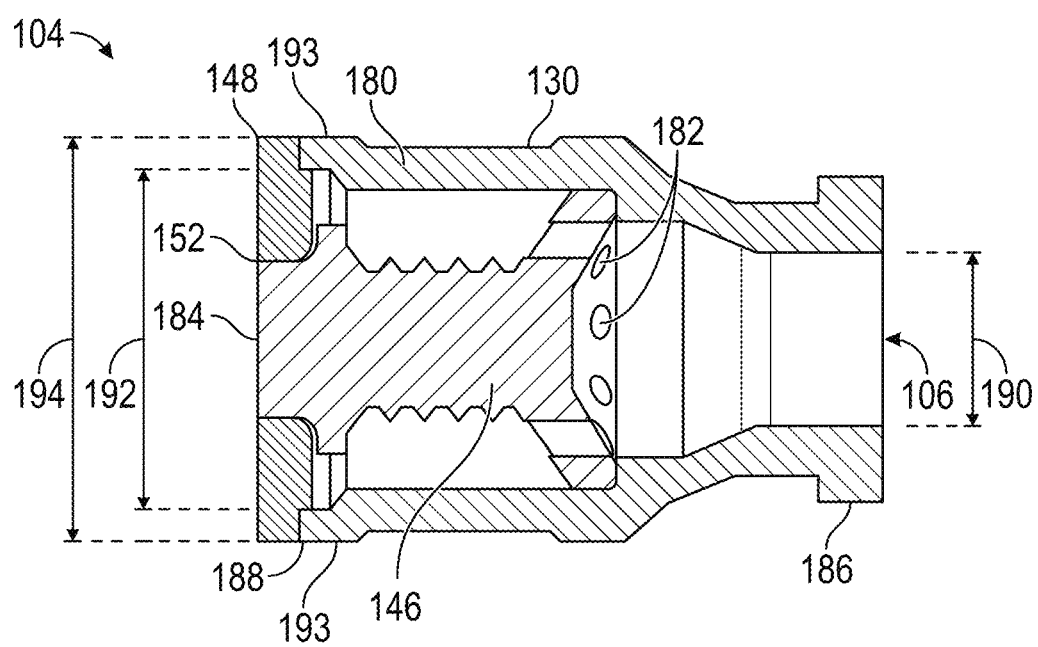
FIG. 6 illustrates a partial cross-sectional view of the connector of the fluid connector assembly, in accordance with aspects of the present disclosure.

FIG. 6 illustrates a partial cross-sectional view of the connector 104 of the fluid connector assembly 100, in accordance with aspects of the present disclosure. As shown, the compressible member 146 is located in a hollow portion of the housing 130 and is at least partially engaged with an inner wall 180 of the housing 130. The compressible member 146 includes openings 182, representative of additional openings (shown, not labeled) of the compressible member 146. While FIG. 6 shows several openings formed in the compressible member 146, the number of openings may vary. For example, in some embodiments, one or more openings may be formed in the compressible member 146. In either event, each opening(s) may include any feature shown and described for the openings 182. Fluid flowing through the fluid inlet 106 may pass through the compressible member 146 via the openings 182. Further, the compressible member 146 includes a protrusion 184 that extends into the opening 152 of the plate 148.

The housing 130 includes two opposing ends. As shown, the housing 130 include an end 186 and an end 188 opposite the end 186. The end 186 of the housing 130, where the fluid inlet 106 is located, includes an inner diameter 190. The end 188 of the housing 130, to which the plate 148 is connected, includes an inner diameter 192 that is greater than the inner diameter 190 of the end 186. Additionally, the end 188 of the housing 130 includes an outer diameter 194. In some embodiments, the outer diameter 194 of the end 188 of the housing 130 is the same as, or at least substantially similar, to a diameter of the plate 148. The outer diameter 194 includes a dimension that allows at least a portion of the plate 148 and at least a portion of the housing 130 to enter the connector 102 (shown in FIG. 5). In this manner, the dimension of the inner diameter 176 of the end 172 (shown in FIG. 5) may be greater than the outer diameter 194 of the end 188 of the housing 130. Also, the dimension of the inner diameter 176 of the end 172 may be greater than the diameter of the plate 148.

Based on the position of the compressible member 146 shown in FIG. 6, the connector 104 prevents fluid flow therethrough. For example, when the protrusion 184 of the compressible member 146 is located in the opening 152 of the plate 148 and when the compressible member 146 engages the plate 148, fluid entering the fluid inlet 106 is blocked from exiting through the end 188 of the housing 130.

In order to promote fluid through the connectors 102 and 104, the respective compressible members can be actuated, or displaced, to uncover respective openings in the connectors 102 and 104.

Figure 7:
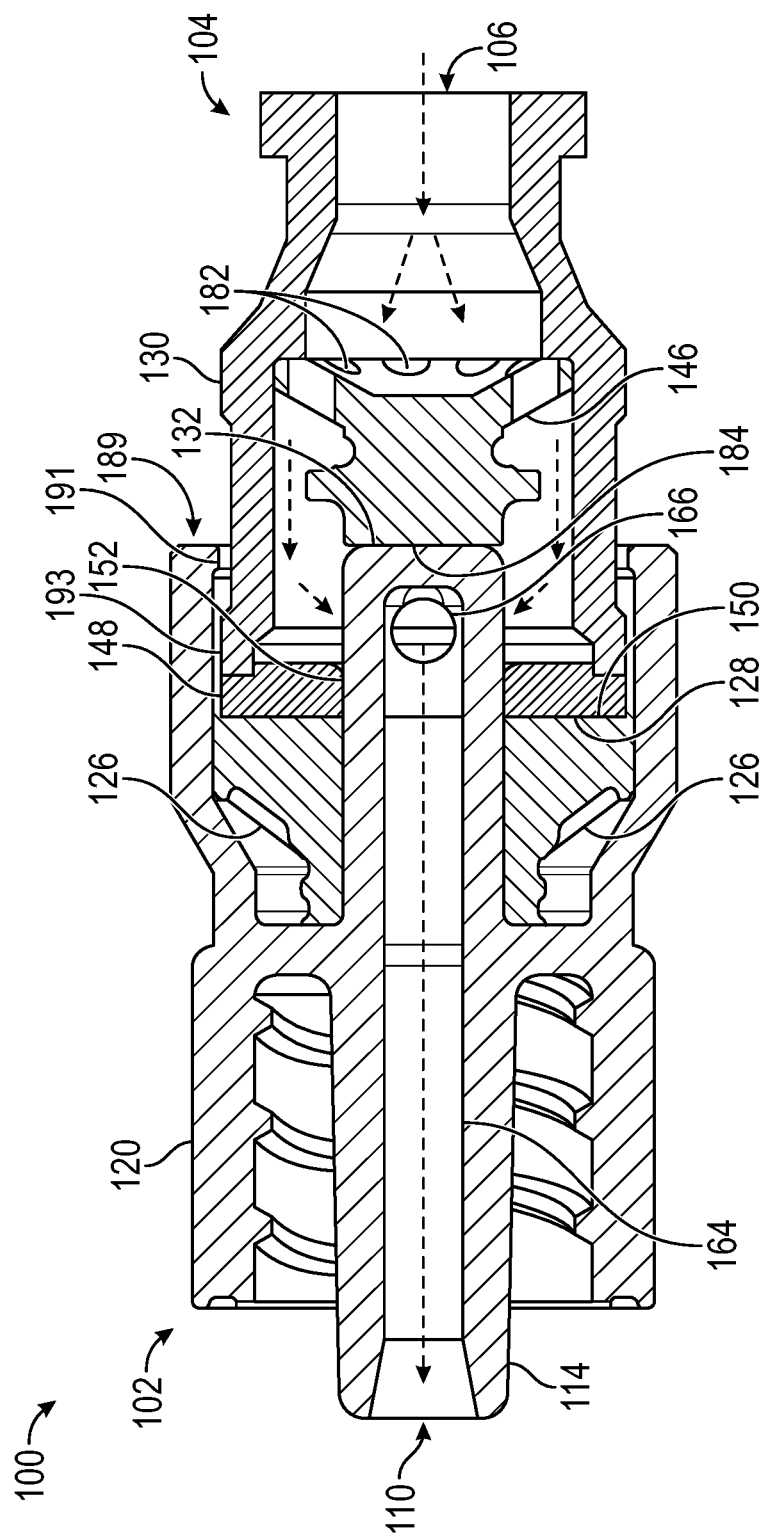
FIG. 7 illustrates a partial cross-sectional view of the fluid connector assembly, showing the connectors and engaged, and further showing actuation of the respective compressible members, in accordance with aspects of the present disclosure.

FIG. 7 illustrates a partial cross-sectional view of the fluid connector assembly 100, showing the connectors 102 and 104 engaged, and further showing actuation of the compressible members 126 and 146, in accordance with aspects of the present disclosure. Based upon the respective dimensions of the outer diameter 194 of the housing 130 (shown in FIG. 6) and the inner diameter 176 of the end 172 of the housing 120 (shown in FIG. 5), the plate 148 can be inserted into the cavity 168 (labeled in FIG. 5) of the housing 120 and the housing 130 can be at least partially inserted into the cavity 168 of the housing 130. The connectors 102 and 104 can remain coupled together by a snap mechanism 189.

The snap mechanism 189 can include a friction or interference fit between engaging ends of the connectors 102, 104. For example, in some embodiments, connector 102 can include an inner rim 191 that extends inward. As depicted in FIG. 7, the inner rim 191 can extend circumferentially, and in some embodiments, it can provide opposing rims 191 separated by slots 122, 124. When the inner rim 191 is separated by slots 122, 124, the housing 120 may be configured to deflect outwardly at the slots to permit a friction or interference fit as connector 104 is inserted into housing 120. Inner rim 191 can include beveled edges to permit sliding engagement with portions of connector 104 as the connector 104 is inserted inside the housing 120. Connector 104 can include an outer rim 193 that extends slightly radially outwardly such that when connector 104 is inserted into housing 120 of connector 102, the outer rim 193 creates a slight deflection of housing 120 as the inner rim 191 passes over outer rim 193. As the connector 104 is further advanced into the housing 120, the housing 120 will be permitted to return slightly or entirely from its deflected state when the inner rim 191 has passed beyond the outer rim 193. The friction fit or interference fit between the inner rim 191 and the outer rim 193 provides the snap mechanism 189 that secures connector 102 with connector 104 when the connectors 102, 104 are coupled together.

The snap mechanism 189 provides a retaining force to maintain the connection/coupling between the connectors 102 and 104 as shown in FIG. 7. The retaining force provided by the snap mechanism 189 may also be equated to a threshold force that maintains the connection/coupling between the connectors 102 and 104. However, when an external force, such as a pulling force provided to one or more of the connectors 102 and 104, is applied to at least one of the connectors 102 and 104 and is greater than the threshold force, the snap mechanism 189 may no longer maintain the connection/coupling between connectors 102 and 104, and the connectors 102 and 104 may decouple from each other. When this occurs, plate 148 and the housing 130 of the connector 104 are removed from the housing 120 of the connector 102.

Upon insertion the housing 120, the plate 148 may engage the compressible member 126 of the connector 102. For example, as shown in FIG. 7, the engagement surface 150 of the plate 148 is engaged with the engagement surface 128 of the compressible member 126. From the perspective of the compressible member 126, an external force is provided by at least the plate 148. Based on the insertion and engagement, the plate 148 provides a force that actuates the compressible member 126. For example, the actuation of the compressible member 126 may include a compression of the compressible member 126. In this manner, the compression of the compressible member 126 causes the compressible member 126 to reduce in size, to move relative to the post 114, and to expose the opening 166 of the post 114. Accordingly, the opening 166 of the post 114 is uncovered by the compressible member 126 and the compressible member 126 no longer provides a seal against fluid entry into the opening 166. Accordingly, the compressible member 126, located in the housing 120, is designed to actuate, e.g., compress, in response to a force received by an external object, or objects, of the connector 104.

At or near the same time of insertion of the insertion of the plate 148 and the housing 130 into the housing 120, the post 114 of the connector 102 engages the compressible member 146 of the connector 102. For example, the closed end 132 of the post 114 engages the protrusion 184 of the compressible member 146. From the perspective of the compressible member 146, an external force is provided by at least the post 114. As the plate 148 and the housing 130 are further inserted into the housing 120, the post 114 provides a force that actuates the compressible member 146. For example, the actuation of the compressible member 146 may include a compression of the compressible member 146, thereby reducing the size of the compressible member 146, forcing the protrusion 184 of the compressible member 146 out of the opening 152 of the plate 148, and causing the compressible member 146 to disengage the plate 148. The disengagement between the compressible member 146 and the plate 148 breaks the seal between the compressible member 146 and the plate 148. Also, the actuation of the compressible member 146 allows the post 114 to pass through the opening 152 of the plate 148 and extend into the housing 130. Moreover, the post 114 passes through the opening 152 of the plate 148 such that the opening 166 of the post 114 also passes through the opening 152 of the plate 148 and is positioned in the housing 130. Accordingly, the compressible member 146, located in the housing 130, is designed to actuate, i.e., compress, in response to a force received by an external object, or objects, of the connector 102.

Based upon the configuration of the fluid connector assembly 100 shown in FIG. 7, a fluid path is established. For example, the arrows within the connectors 102 and 104 show an exemplary fluid path, including respective fluid paths through the connectors 102 and 104. The direction of the arrows represents a downstream, or at least a generally downstream, path through the connectors 102 and 104. Accordingly, a fluid, including a medical fluid, can pass through the fluid connector assembly 100 downstream from the connector 104 to the connector 102. As shown, fluid can enter the fluid inlet 106 of the housing 130 and subsequently pass through the compressible member 146 by way of the openings 182 of the compressible member 146. The fluid can then pass through the opening 166 of the post 114, and then through the channel 164 of the post 114. The fluid can exit the fluid connector assembly 100 through the fluid outlet 110 of the housing 120.

Figure 8:
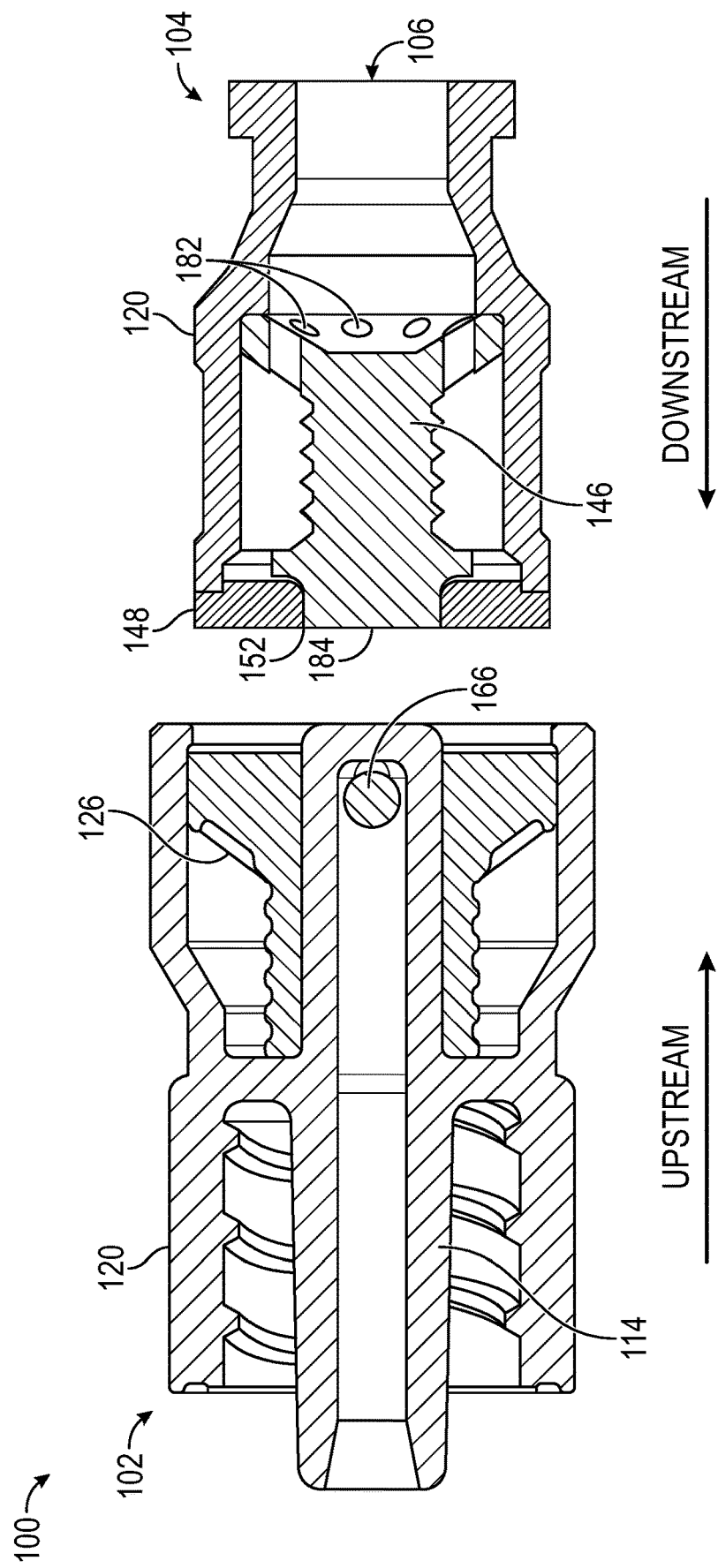
FIG. 8 illustrates a partial cross-sectional view of the fluid connector assembly, showing the connectors decoupled from each other and the respective fluid paths of the connectors sealed off based on the compressible members, in accordance with aspects of the present disclosure.

FIG. 8 illustrates a partial cross-sectional view of the fluid connector assembly 100, showing the connectors 102 and 104 decoupled from each other and the respective fluid paths of the connectors sealed off based on the compressible members 126 and 146, in accordance with aspects of the present disclosure. The decoupling of the connectors 102 and 104 may result from an external force applied to one or more of the connectors 102 and 104, where the external force exceeds the threshold force provided by the snap mechanism that maintains a connection between the connectors 102 and 104.

As shown, the connector 104 is removed from the connector 102. When the plate 148 begins to exit the housing 120, the force provided by the plate 148 decreases and the compressible member 126 decompresses. When the plate 148 disengages with the compressible member 126, the compressible member 126 expands and returns to its original shape, and again covers and seals the opening 166. As a result, fluid is unable to flow upstream through the connector 102 and pass through the opening 166 of the post 114.

Also, as the plate 148 and the housing 130 begin to exit from the housing 120, the force provided by the post 114 decreases and the compressible member 146 decompresses. When the post 114 disengages from the compressible member 146, the compressible member 146 expands and returns to its original shape, resulting in the protrusion 184 of the compressible member 146 moving into the opening 152 of the plate 148, and the compressible member 146 and the plate 148 sealing the opening 152. As a result, fluid is unable to flow downstream through the connector 104 and pass through the opening 152.

Each of the compressible members 126 and 146 can be used as a valve to regulate fluid through the fluid connector assembly 100. Based on their elastic, springlike properties, each of the compressible members 126 and 146 automatically return to their respective shapes when external forces are no longer acting on them. Beneficially, the compressible members 126 and 146 spring back in response to a decoupling between the connectors 102 and 104 to provide a relatively quick sealing effect. Accordingly, blood losses, IV fluid losses, and medical delivery delays can be limited or prevented, based on one or more properties of the compressible members 126 and 146, when integrating the connector assembly 100 into an IV set and catheter.

Figure 9:
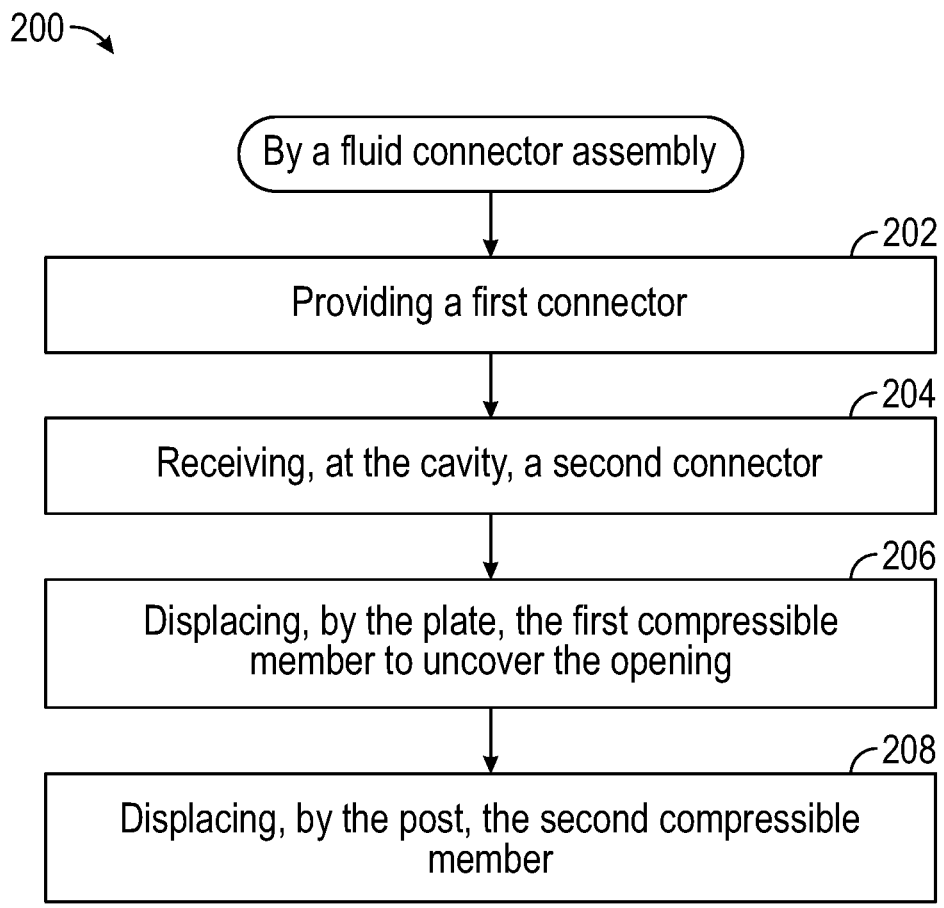
FIG. 9 illustrates a flowchart showing a method for regulating a fluid for an intravenous application, in accordance with aspects of the present disclosure.

FIG. 9 illustrates a flowchart 200 showing a method for regulating a fluid for an intravenous application, in accordance with aspects of the present disclosure. Fluid connector assemblies described herein may carry one or more steps of the method shown and described in the flowchart 200.

In step 202, a first connector is provided. In some embodiments, the first connector includes a post that defines a channel. The first connector may further include a first compressible member surrounding the post. In some embodiments, the first compressible member includes a bellow. Further, the first compressible member may elastically compress based on an external force and return to its original shape after the external force is removed. The first connector may further include an opening formed in the post. In some embodiments, the opening is fluidly connected to the channel. The first connector may further include a cavity.

In step 204, a second connector is received at the cavity. The second connector may include a plate. The second connector may further include a second compressible member. In some embodiments, the second compressible member includes a bellow. In these embodiments, the bellow may include a spider bellow. Further, the compressible member may elastically compress based on an external force and return to its original shape after the external force is removed. Also, the cavity of the first connector includes a size and shape capable of receiving, or at least partially receiving, the second connector, including the plate of the second connector.

In step 206, the first compressible member is displaced by the plate to uncover the opening. The displacement may include a compression of the first compressible member by the plate. Prior to the displacement, the first compressible member may seal the opening. However, as a result of the displacement of the first compressible member, the opening is no longer sealed by the first compressible member.

In step 208, the second compressible member is displaced by the post. The displacement of the second compressible member allows the fluid to pass through the opening. Similar to the first compressible member, the displacement of the second compressible member may include a compression of the second compressible member by the post. The first and second compressible members may decompress and return to their original, respective shapes, when the first and second compressible members are no longer acted upon and displaced by their respective objects.

Figure 10:
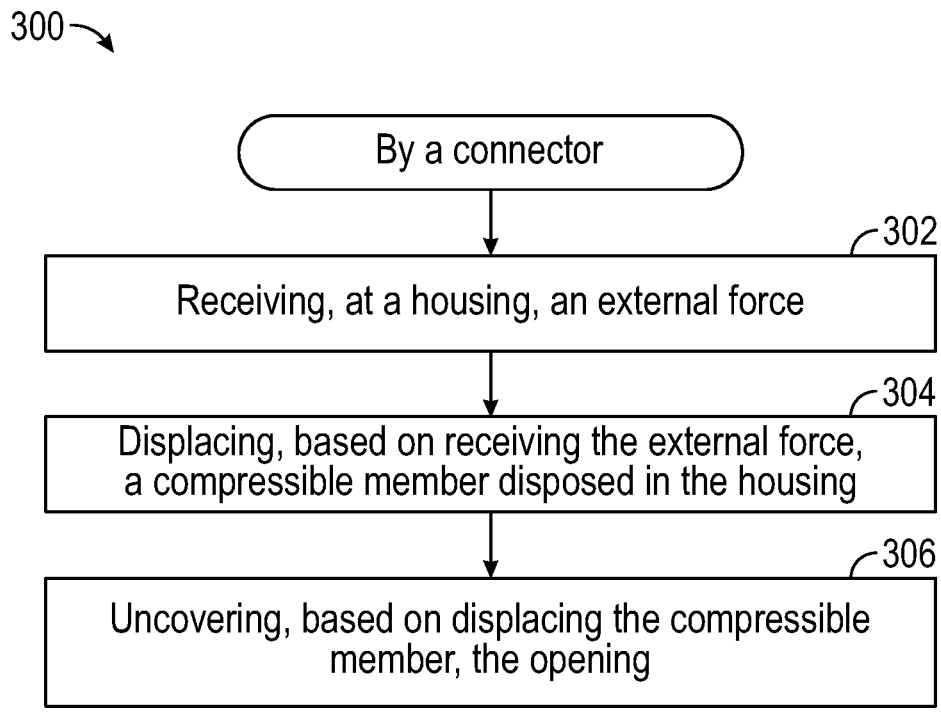
FIG. 10 illustrates a flowchart showing a method for regulating a fluid, in accordance with aspects of the present disclosure.

FIG. 10 illustrates a flowchart 300 showing a method for regulating a fluid, in accordance with aspects of the present disclosure. At least some connectors described herein may carry one or more steps of the method shown and described in the flowchart 300. For example, the connector 102 (shown in FIG. 2) can carry out one or more steps of the method shown and described in the flowchart 300.

In step 302, an external force is received at a housing of the connector. The housing may include a post that includes an opening. The external force may be provided by an additional connector designed to couple with the connector. Moreover, the external force may be provided by a component (e.g., plate) of the additional connector.

In step 304, a compressible member disposed in the housing is displaced based on receiving the external force. In some embodiments, the compressible member includes a bellow. The displacement may include a compression of the compressible member by the additional connector, including a component thereof. Further, the compressible member may elastically compress based on an external force and return to its original shape after the external force is removed.

In step 306, the opening is uncovered based on displacing the compressible member. Prior to the displacement, the compressible member may seal the opening. However, based on the displacement of the compressible member, the opening is no longer sealed by the compressible member. The compressible member may decompress and return to its original, uncompressed shape, when the compressible member is no longer acted upon and displaced by the additional connector, including a component thereof. Accordingly, the compressible member can subsequently cover and seal the opening.

Figure 11:
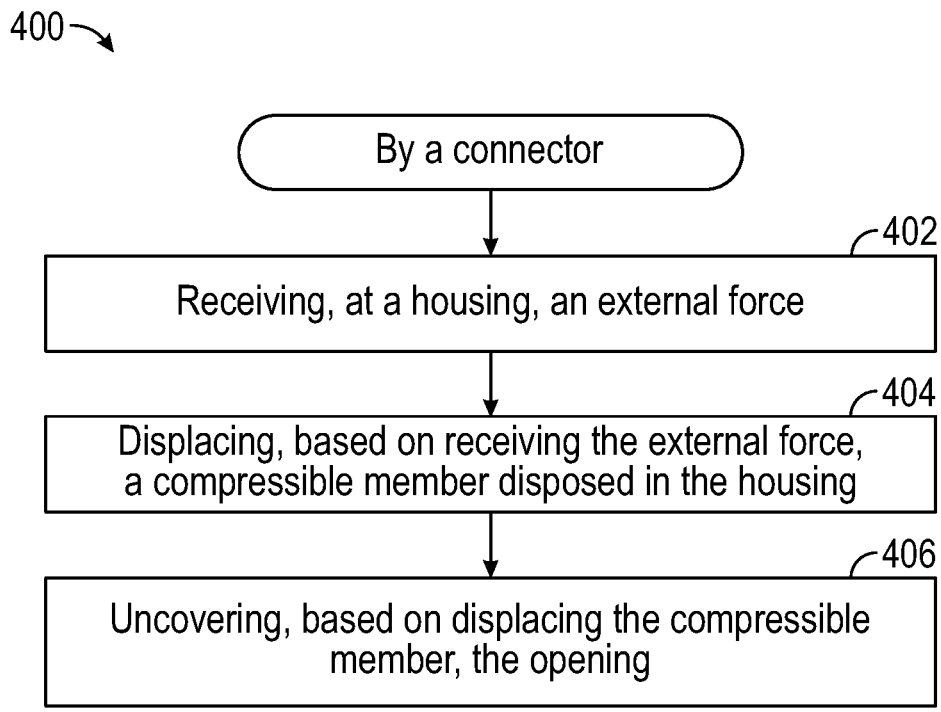
FIG. 11 illustrates a flowchart showing a method for regulating a fluid, in accordance with aspects of the present disclosure.

FIG. 11 illustrates a flowchart 400 showing a method for regulating a fluid, in accordance with aspects of the present disclosure. At least some connectors described herein may carry one or more steps of the method shown and described in the flowchart 400. For example, the connector 104 (shown in FIG. 2) can carry out one or more steps of the method shown and described in the flowchart 400.

In step 402, an external force is received by a housing of the connector. The housing may include a plate that includes an opening. The external force may be provided by an additional connector designed to couple with the connector. Moreover, the external force may be provided by a component (e.g., post) of the additional connector.

In step 404, a compressible member disposed in the housing is displaced based on receiving the external force. In some embodiments, the compressible member includes a bellow. In these embodiments, the bellow may include a spider bellow. The displacement may include a compression of the compressible member by the additional connector, including a component thereof. Further, the compressible member may elastically compress based on an external force and return to its original shape after the external force is removed.

In step 406, the opening is uncovered based on displacing the compressible member. Prior to the displacement, the compressible member may, in combination with the plate, seal the opening. However, based on the displacement of the compressible member, the opening is no longer sealed by the compressible member, as the compressible member is no longer engaged with the plate. The compressible member may decompress and return to its original, uncompressed shape, when the compressible member is no longer acted upon and displaced by the additional connector, including a component thereof. Accordingly, the compressible member can subsequently engage the plate and seal the opening.

The features of the present disclosure provide first and second compressible members that can be used as valves to regulate a fluid pathway therebetween. The first and second compressible members are located in a first and a second connector, respectively. If the first and second connectors are separated, whether unintentionally or intentionally, the fluid pathway for each of the first and second compressible members become closed or obstructed to prevent fluid loss therefrom. The features of the present disclosure also provide that upon separation of the first and second compressible members, any of the first and second compressible members can be cleaned and disinfected, and the first and second compressible members can be once again coupled together to form a fluid pathway therebetween.

Illustration of Subject Technology as Clauses

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1, clause 11, clause 17, clause, clause 23, clause 26, or clause 29. The other clauses can be presented in a similar manner.

Clause 1. A fluid connector assembly, comprising: a first connector, comprising: a first housing comprising a cavity, a post disposed in the first housing, the post comprising an opening, and a compressible member surrounding the post; and a second connector configured to couple with the first connector, the second connector comprising: a second housing, and a plate coupled with the second housing, wherein when the second housing is positioned in the cavity, the plate displaces the compressible member and exposes the opening.

Clause 2. The fluid connector assembly described above, wherein when the second housing is removed from the cavity, the compressible member seals the opening.

Clause 3. The fluid connector assembly described above, wherein: the opening comprises a first opening, the plate comprises a second opening, and when the second housing is positioned in the cavity, the post is positioned in the second opening.

Clause 4. The fluid connector assembly described above, wherein: the compressible member comprises a first compressible member, the second connector further comprises a second compressible member disposed in the second housing, and when the second housing is positioned in the cavity, the post displaces the second compressible member.

Clause 5. The fluid connector assembly described above, further comprising a channel formed in the post, the channel fluidly connected to the first opening, first opening, the second opening, and the channel define a fluid path.

Clause 6. The fluid connector assembly described above, further comprising a third opening formed in the second compressible member, wherein the third opening further defines the fluid path.

Clause 7. The fluid connector assembly described above, wherein when the plate is disengaged from the first compressible member, the second compressible member seals the second opening.

Clause 8. The fluid connector assembly described above, wherein: the second housing comprises a fluid inlet, the first housing comprises a fluid outlet, and, the fluid inlet and the fluid outlet further define the fluid path.

Clause 9. The fluid connector assembly described above, wherein: the second connector is held in the cavity by a threshold force, and responsive to an external force, greater than the threshold force, applied to at least one of the first connector and the second connector that removes the second housing from the cavity: the first compressible member seals the first opening, and the second compressible member seals the second opening.

Clause 10. The fluid connector assembly described above, wherein the second compressible member is movable relative to the plate.

Clause 11. A connector suitable for use with intravenous applications, the connector comprising: a housing; a post disposed within the housing, the post defining a channel; an opening formed in the post, the opening fluidly connected to the channel; a compressible member surrounding the post, wherein: responsive to an external force displacing the compressible member, the compressible member uncovers the opening, and when the external force is removed, the compressible member seals the opening.

Clause 12. The connector described above, further comprising a cavity defined by the housing and the post, wherein the compressible member uncovers the opening based on an external object entering the cavity and providing the external force.

Clause 13. The connector described above, further comprising a wall disposed in the housing, wherein the post is integrated with the wall and the channel passes through the wall.

Clause 14. The connector described above, wherein: the cavity comprises a first cavity, and the body and the post further define a second cavity separated from the first cavity by the wall.

Clause 15. The connector described above, wherein: the housing holds the external object in the cavity by a threshold force, and responsive to an external force, greater than the threshold force, applied to at least one of the housing and the external object, the housing disengages from the external object at the cavity and the compressible member seals the opening.

Clause 16. The connector described above, wherein the post is positioned in the cavity such that a second compressible member of the external object is compressed by the post when the external object is positioned in the cavity.

Clause 17. A connector suitable for use with intravenous applications, the connector comprising: a housing; a compressible member disposed in the housing; and a plate coupled with the housing, the plate defining an opening, wherein responsive to an external object entering the opening and displacing the compressible member, the compressible member uncovers the opening, and when the external object is removed, the compressible member seals the opening.

Clause 18. The connector described above, wherein the housing defines a fluid inlet, and when the compressible member is displaced to uncover the opening, the compressible member permits the fluid entering the fluid inlet to pass through the opening.

Clause 19. The connector described above, wherein: the opening defines a first opening, the compressible member defines a second opening, and when the compressible member uncovers the first opening, a fluid path is established by the fluid inlet, the first opening, and the second opening.

Clause 20. The connector described above, wherein the compressible member is movable with respect to the plate.

Clause 21. The connector described above, wherein the compressible member comprises a protrusion, and when the compressible member engages the plate, the protrusion is positioned in the opening.

Clause 22. The connector of described above, wherein: when the body is disposed in an external body, the body is held by a threshold force, and responsive to an external force, greater than the threshold force, applied to at least one of the body and the external body, the body is disengaged from the external body and the compressible member covers the opening.

Clause 23. A method for regulating a fluid for an intravenous application, the method comprising, by a fluid connector assembly: providing a first connector, the first connector comprising: a post that defines a channel, a first compressible member surrounding the post, an opening formed in the post, the opening fluidly connected to the channel, and a cavity; and receiving, at the cavity, a second connector, the second connector comprising: a plate, and a second compressible member; and displacing, by the plate, the first compressible member to uncover the opening; and displacing, by the post, the second compressible member, thereby allowing the fluid to pass through the opening.

Clause 24. The method described above, further comprising positioning the post, based on receiving the second connector, at least partially in the second connector.

Clause 25. The method described above, further comprising removing, by an external force, the second connector from the cavity, thereby causing the first compressible member to seal the opening.

Clause 26. A method for regulating a fluid, the method comprising, by a connector: receiving, at a housing, an external force, the housing comprising a post that includes an opening; displacing, based on receiving the external force, a compressible member disposed in the housing; and uncovering, based on displacing the compressible member, the opening.

Clause 27. The method described above, wherein displacing the compressible member comprising compressing the compressible member.

Clause 28. The method described above, wherein compressing the compressible member comprising moving the compressible member relative to the post.

Clause 29. A method for regulating a fluid, the method comprising, by a connector: receiving, at a housing, an external force, the housing comprising a plate that includes an opening; displacing, based on receiving the external force, a compressible member disposed in the housing; and uncovering, based on displacing the compressible member, the opening.

Clause 30. The method described above, wherein displacing the compressible member comprising compressing the compressible member.

Clause 31. The method described above, wherein compressing the compressible member comprising moving the compressible member relative to the plate.

Clause 33. The method described above, wherein displacing the compressible member comprising disengaging the compressible member from the plate.

Clause 34. The method described above, further comprising removing, based on displacing the compressible member, a protrusion of the compressible member from the opening.

Further Considerations

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A fluid connector assembly, comprising:
    a first connector, comprising:
        a first housing comprising a cavity and a slot,
        a post disposed in the first housing, the post comprising an opening, and
        a compressible member surrounding the post; and
    a second connector configured to couple with the first connector, the second connector comprising:
        a second housing comprising a pin, and
        a plate coupled with the second housing, wherein the slot permits the first housing to deflect outward when the second housing is inserted into the cavity, and wherein when the second housing is positioned in the cavity, the pin is positioned in the slot and the plate displaces the compressible member and exposes the opening.

2. The fluid connector assembly of claim 1, wherein when the second housing is removed from the cavity, the compressible member seals the opening.

3. The fluid connector assembly of claim 1, wherein:
    the opening comprises a first opening,
    the plate comprises a second opening, and
    when the second housing is positioned in the cavity, the post is positioned in the second opening.

4. The fluid connector assembly of claim 3, wherein the second connector further comprises a second compressible member having a protrusion configured to extend into the second opening.

5. The fluid connector assembly of claim 3, wherein:
    the compressible member comprises a first compressible member,
    the second connector further comprises a second compressible member disposed in the second housing, and
    when the second housing is positioned in the cavity, the post displaces the second compressible member.

6. The fluid connector assembly of claim 5, further comprising a channel formed in the post, the channel fluidly connected to the first opening, first opening, the second opening, and the channel define a fluid path.

7. The fluid connector assembly of claim 6, further comprising a third opening formed in the second compressible member, wherein the third opening further defines the fluid path.

8. The fluid connector assembly of claim 6, wherein when the plate is disengaged from the first compressible member, the second compressible member seals the second opening.

9. The fluid connector assembly of claim 6, wherein:
    the second housing comprises a fluid inlet,
    the first housing comprises a fluid outlet, and
    the fluid inlet and the fluid outlet further define the fluid path.

10. The fluid connector assembly of claim 6, wherein:
    the second connector is held in the cavity by a threshold force, and
    responsive to an external force, greater than the threshold force, applied to at least one of the first connector and the second connector that removes the second housing from the cavity:
        the first compressible member seals the first opening, and the second compressible member seals the second opening.

11. The fluid connector assembly of claim 6, wherein the second compressible member is movable relative to the plate.

12. A method for regulating a fluid for an intravenous application, the method comprising, by a fluid connector assembly:
providing a first connector, the first connector comprising:
a first housing comprising a slot and a post, the post defining a channel,
a first compressible member surrounding the post,
an opening formed in the post, the opening fluidly connected to the channel, and a cavity; and
receiving, at the cavity, a second connector such that the housing deflects outward, the second connector comprising:
a second housing comprising a pin and a plate, and
a second compressible member; and
receiving the pin within the slot;
displacing, by the plate, the first compressible member to uncover the opening; and
displacing, by the post, the second compressible member, thereby allowing the fluid to pass through the opening.

13. The method of claim 12, further comprising positioning the post, based on receiving the second connector, at least partially in the second connector.

14. The method of claim 12, further comprising removing, by an external force, the second connector from the cavity, thereby causing the first compressible member to seal the opening.

15. The method of claim 12, wherein displacing the first compressible member comprising compressing the first compressible member.

16. The method of claim 15, wherein compressing the first compressible member comprising moving the first compressible member relative to the post.

17. The method of claim 12, wherein displacing the second compressible member comprising compressing the second compressible member.

18. The method of claim 17, wherein compressing the second compressible member comprising moving the second compressible member relative to the plate.

19. The method of claim 12, wherein displacing the second compressible member comprising disengaging the second compressible member from the plate.

20. The method of claim 12, further comprising removing, based on displacing the second compressible member, a protrusion of the second compressible member from an opening of the plate.

* * * * *